(12) United States Patent
Suddaby

(10) Patent No.: US 6,224,604 B1
(45) Date of Patent: May 1, 2001

(54) EXPANDABLE ORTHOPEDIC DRILL FOR VERTEBRAL INTERBODY FUSION TECHNIQUES

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 0 days.

(21) Appl. No.: 09/365,224

(22) Filed: Jul. 30, 1999

(51) Int. Cl.[7] .................................................. A61B 17/56
(52) U.S. Cl. ............................................ 606/80; 408/158
(58) Field of Search ................................. 606/29, 80, 81, 606/84; 408/147, 158, 161

(56) References Cited

U.S. PATENT DOCUMENTS

| | | | |
|---|---|---|---|
| 2,616,103 | * 11/1952 | Stecher | 408/158 |
| 2,694,321 | * 11/1954 | Riza | 408/158 |
| 4,819,744 | 4/1989 | Caswell. | |
| 5,062,845 | 11/1991 | Kuslich et al. . | |
| 5,445,639 | 8/1995 | Kuslich et al. . | |

* cited by examiner

*Primary Examiner*—Michael H. Thaler
*Assistant Examiner*—William Lewis
(74) *Attorney, Agent, or Firm*—Shoemaker and Mattare, LTD

(57) ABSTRACT

An expandable orthopedic drill includes a shaft provided with a handle at is proximal end. Several cutters are supported around the hub by a linkage which maintains the edges of the cutters at a predetermined angle to the axis of the tool. The cutters are driven outward from the shaft, expanding the effective size of the drill, by means of a sleeve. The sleeve is driven along the shaft by turning a nut engaged with threads on the shaft. Tapered holes may be produced by changing the lengths of the links.

6 Claims, 8 Drawing Sheets

EXPANDABLE ORTHOPEDIC DRILL FOR VERTEBRAL INTERBODY FUSION TECHNIQUES

BACKGROUND OF THE INVENTION

This invention relates to an expandable orthopedic drill for facilitating placement of grafts of bone and/or intervertebral implant devices, thereby facilitating the development of a bony union between them and thus long term spinal stability.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures, discs, composed of fibrous tissue and cartilage, which are compressible and act as shock absorbers for sudden downward forces on the upright column. The discs allow the bones to move independently of each other, as well. The repetitive forces which act on these intervertebral discs during day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities, disproportionately affect the more highly mobile areas of the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, may spinal surgeons have found that interbody fusion using bone alone has an unacceptably high rate of bone graft migration or even expulsion or nonunion due to structural failure of the bone or residual degrees of motion that retard or prohibit bony union. Intervertebral prostheses in various forms have therefore been used to provide immediate stability and to protect and preserve an environment that fosters growth of grafted bone such that a structurally significant bony fusion can occur.

A limitation of present interbody fusion techniques is that the vertebral bodies are distracted prior to the drilling of the end plates, necessitating a large diameter drill in situations where ligamentous laxity permits a wide distraction of the intervertebral space. A large diameter drill in turn requires greater retraction of neural or vascular elements, thereby increasing traction-related complication rates. Large diameter drills are also counter-productive for situations requiring endoscopic or "minimal access" techniques.

The present invention allows insertion of the drill into an undistracted disc space such that the drilling to prepare the end plates can be done by an instrument that expands wholly within the protective confines of the disc space without requiring significant distraction of vertebral body elements. By doing this, neural and vascular elements are protected from injury by the cutting surface of the drill and minimal retraction of these elements is required because distraction of the space is not required. In addition, only a single instrument is required to adapt for any size disc space, in contrast to present techniques which require a variety of drills that increase in diameter by 2 mm increments. By varying the lengths of links supporting the cutters, the cutting angle of the drill can be altered to facilitate the production of fluted or angled disc spaces in extremely kyphotic or lordotic spines. In addition, the cutting edge of the drill is serrated to maximize the surface area of the cut bone to promote bony union.

SUMMARY OF THE INVENTION

It is the object of this invention to provide an expandable orthopedic drill for vertebral interbody fusion techniques that can be utilized for anterior, posterior and lateral approaches, as well as for endoscopic and minimally invasive applications.

It is also the object of this invention that the orthopedic drill be simple to use in clinical practice and adaptable to the complex pathology of the human spine.

These and other objects are achieved by an expandable orthopedic drill which includes a shaft having a handle at its proximal end and several cutters supported around its distal end. The cutters are attached to the shaft by linkages which maintain the edges of the cutters at a predetermined angle to the axis of the tool. The cutters are driven outward from the shaft, or brought inward toward it, by means of a sleeve. The sleeve is driven along the shaft turning a nut that engages threads on the shaft so that it can pull or push the sleeve, depending on the direction the nut is turned. Tapered holes are produced by altering the lengths of the links.

BRIEF DESCRIPTION OF THE DRAWINGS

In the accompanying drawings.

DESCRIPTION OF THE PREFERRED EMBODIMENT

Figure 1:
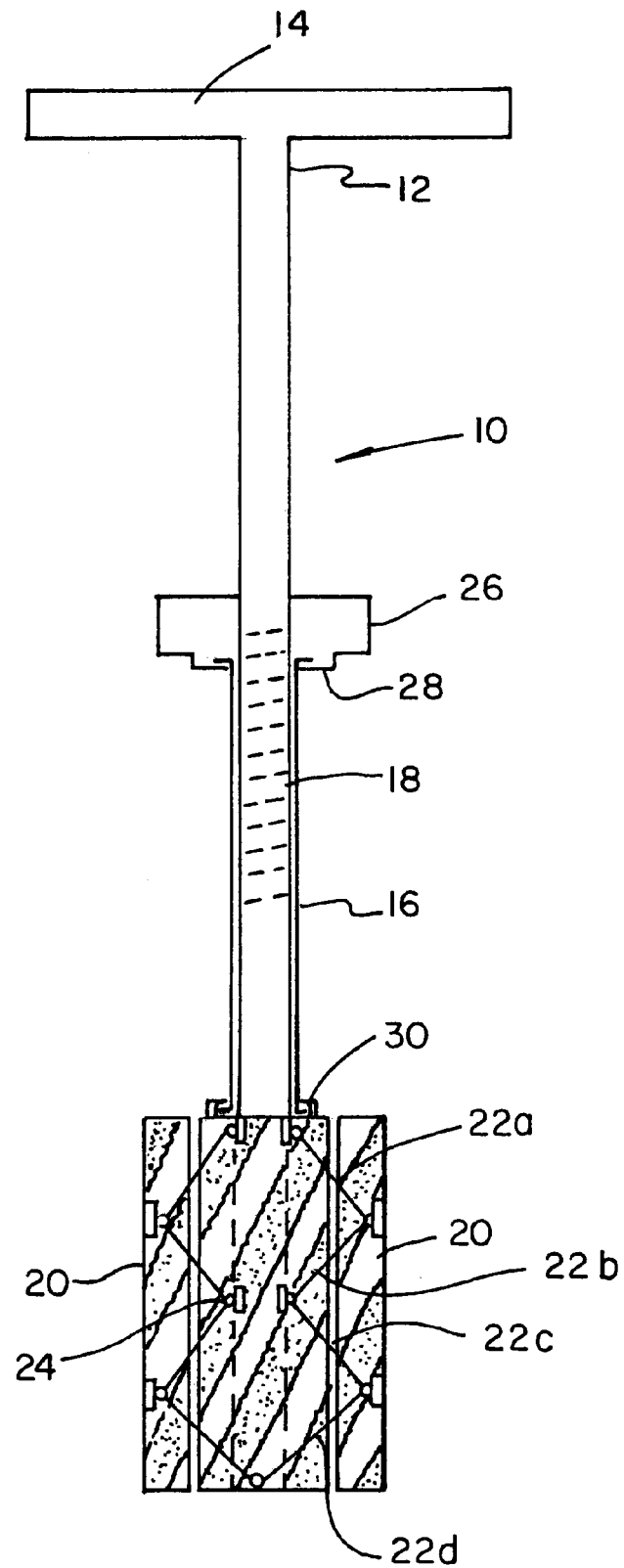
FIG. 1 is a sectional view on a vertical plane of a drill embodying the invention, with its cutters shown retracted.
Figure 2:
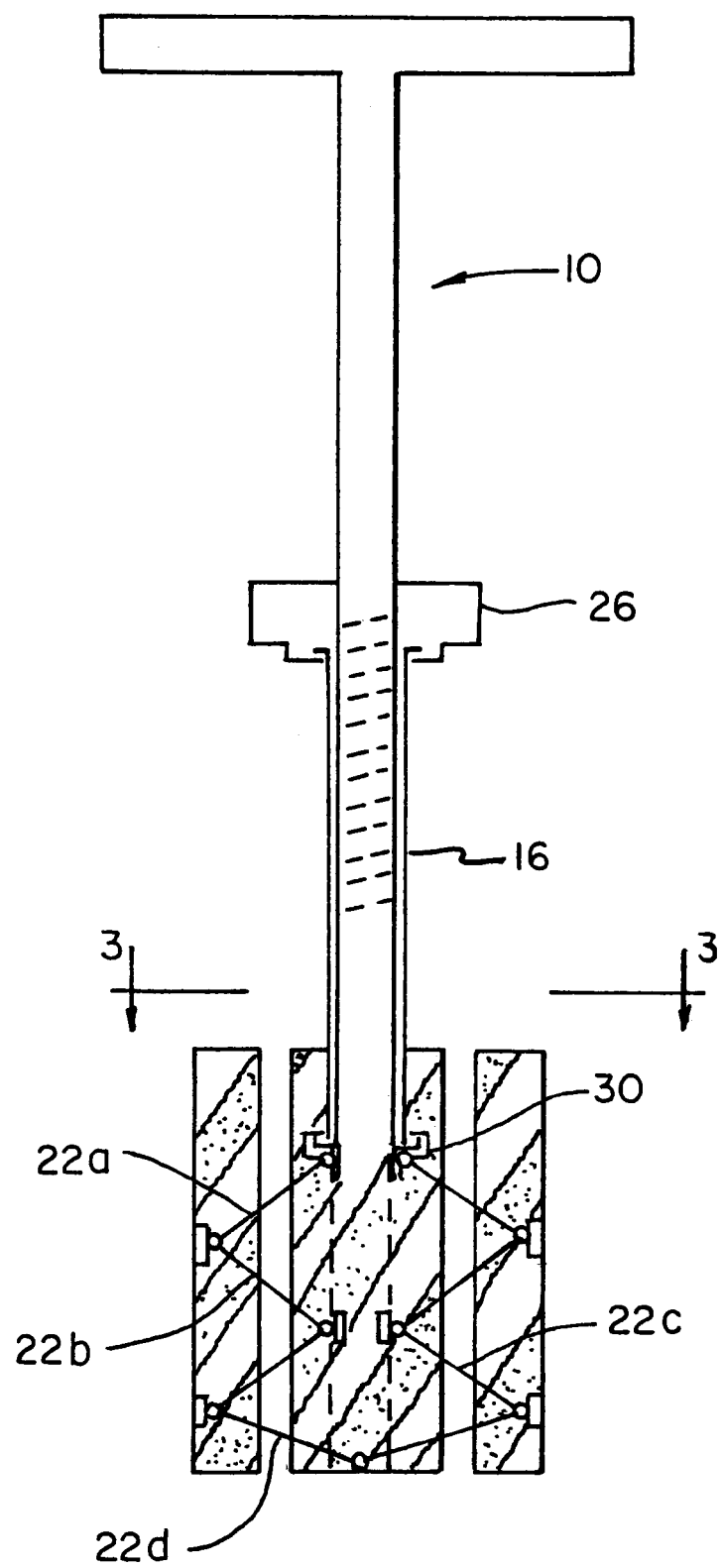
FIG. 2 is a view like FIG. 1, showing the cutters expanded.

An orthopedic drill embodying the invention comprises a shaft 10 having a square proximal end 12 upon which a T-handle 14 is mounted. The shaft is surrounded by a sleeve 16, which can move lengthwise with respect to the shaft. The shaft has helical threads 18 at its middle.

The drill's head comprises several (e.g., four) cutters 20, each of which is supported at the distal end of the shaft by a linkage comprising links 22a, 22b, 22c, 22d. The radially outer ends of the four links are pinned to the cutters. The inner end of the bottom-most links 22d are pinned to the shaft near its distal end. The radially inward ends of the middle two links 22b and 22c are pinned to a sliding collar 24 or the like. The radially inward ends of the upper links 22a are pinned to the distal end of the sleeve. Each of the pin connections permits hinging movement of the links.

The sleeve is move along the shaft in either direction by means of a nut having a rotary connection 28 to the proximal end of the sleeve. The internal helical threads (not shown) of the nut engage the external threads 18 on the shaft, so that turning the nut clockwise advances the sleeve, and counter-clockwise movement retracts it. The rotary coupling keeps the nut 26 and the sleeve 16 together. The rotary coupling may be as simple as a rib on one part rotating within a groove on the other, as suggested in FIG. 1, or a more elaborate structure like a bearing. A similar rotary connection 30 is provided at the bottom of the sleeve, this coupling being connected to the uppermost link pin connection.

Figure 3:
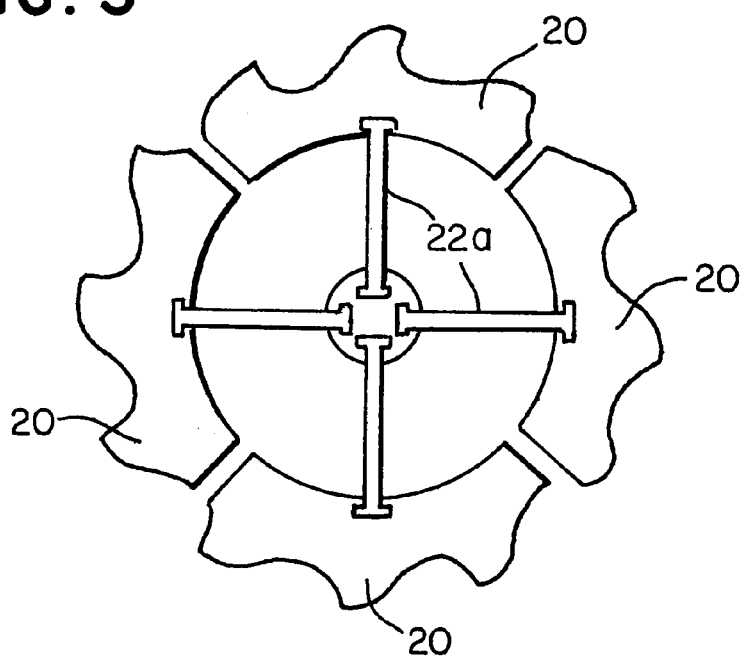
FIGS. 3 and 4 are sectional plan views of the drill, taken on the line 3—3 in FIG. 2, showing the drill contracted and expanded, respectively.
Figure 4:
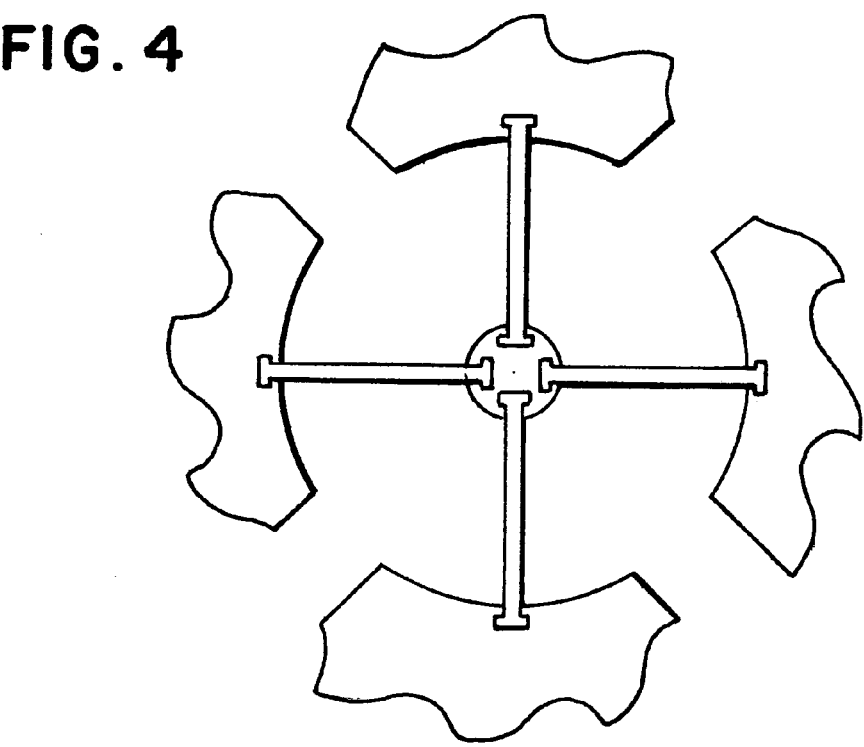
Figure 5:
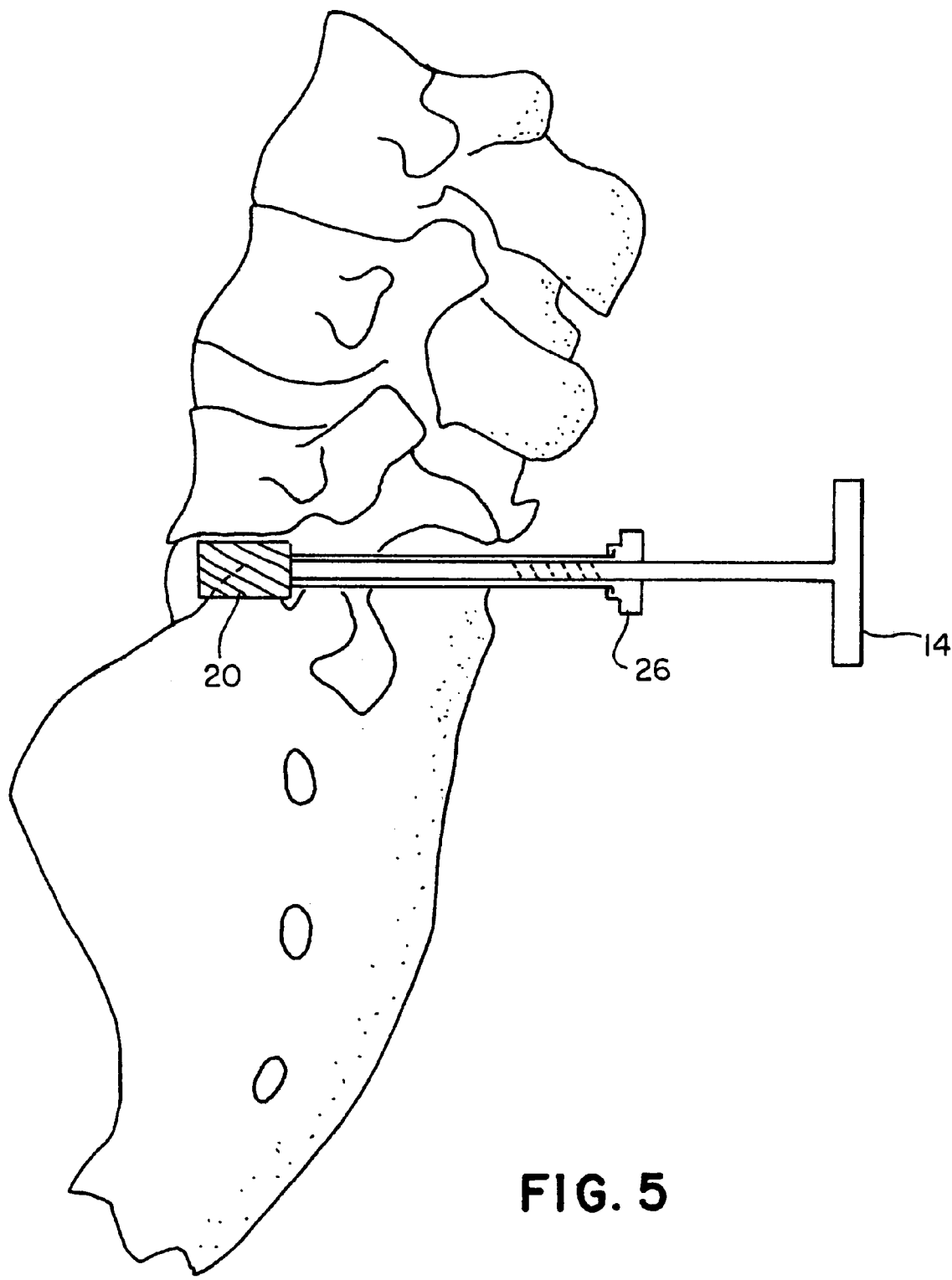
FIG. 5 is a side elevation of the drill, unexpanded, in a disc interspace in a spinal column.
Figure 6:
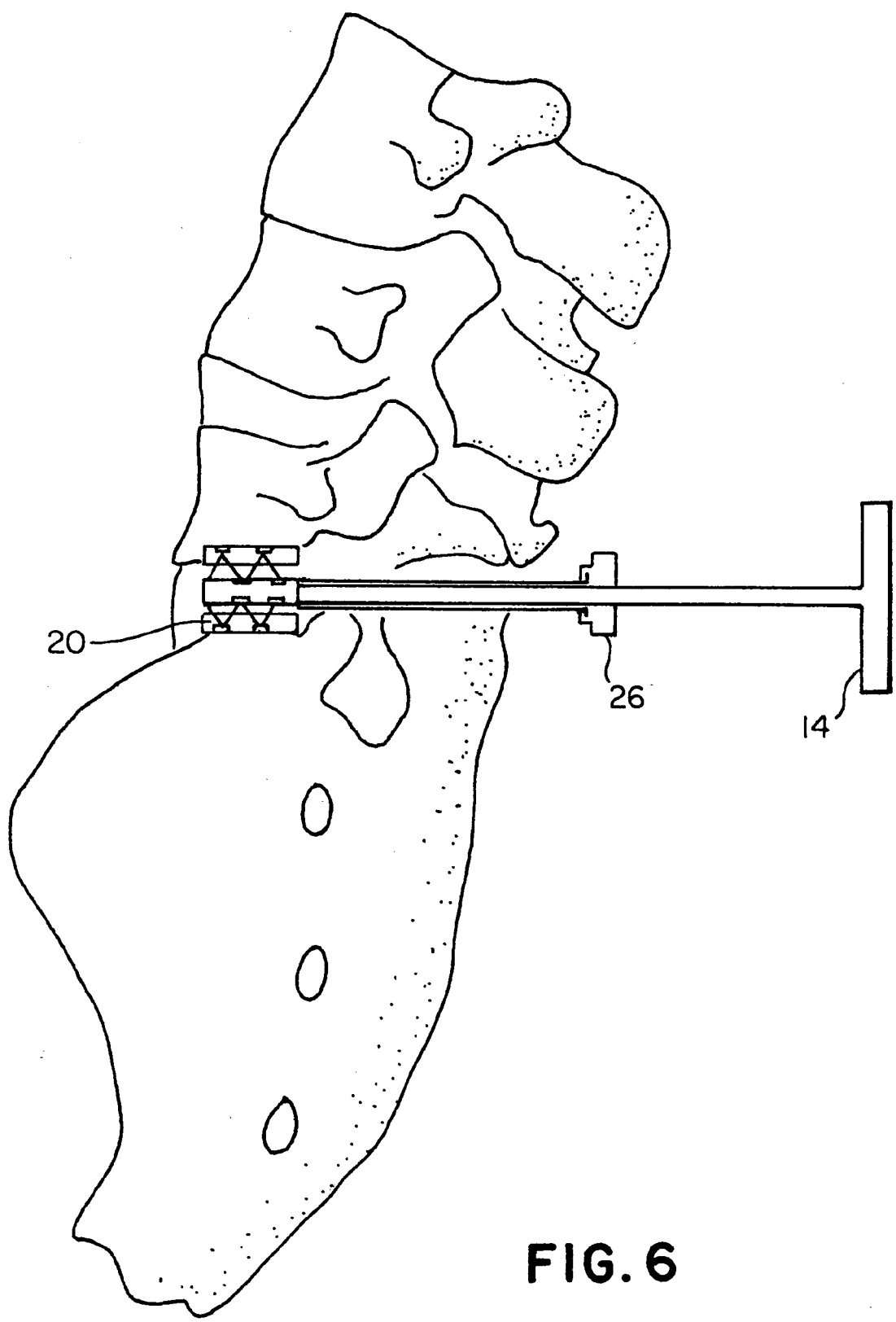
FIG. 6 is a view like FIG. 5, showing the drill expanded in the disc interspace.

One can see the cross-section of the cutters in FIGS. 3 and 4, which also illustrate the expansibility of the drill. The contour and surface finish of the cutting edge may vary, according to the intended result. Preferably, the edges of the cutters are serrated as illustrated to encourage rapid bone regrowth.

In operation, the surgeon first drills a small diameter hole through the vertebral elements. This may be done with a conventional drill, or with the drill described above, in its contracted state. To enlarge the hole, with the expandable drill situated at the bottom of the hole, the nut is turned clockwise. As the nut moves the sleeve along the shaft, the reduction in distance between the distal ends of the sleeve and the shaft causes the links to drive the cutters outward, enlarging the hole as the drill is rotated further. Once the hole is the desired size, the nut is unthreaded to retract the cutters, and the drill is removed from the hole.

Figure 7A:
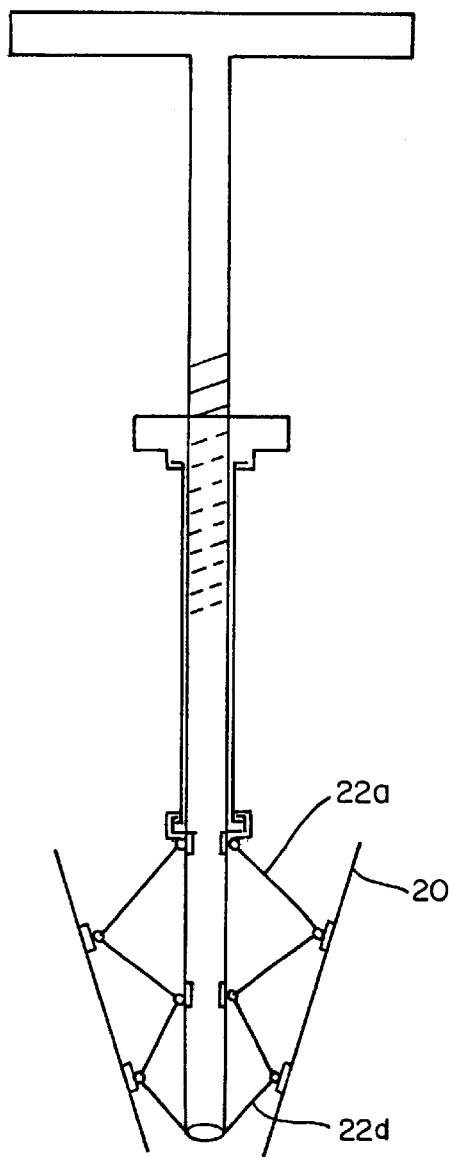
FIGS. 7a and 7b show variations of the invention in which the drill is adapted to drill tapered holes.
Figure 7B:
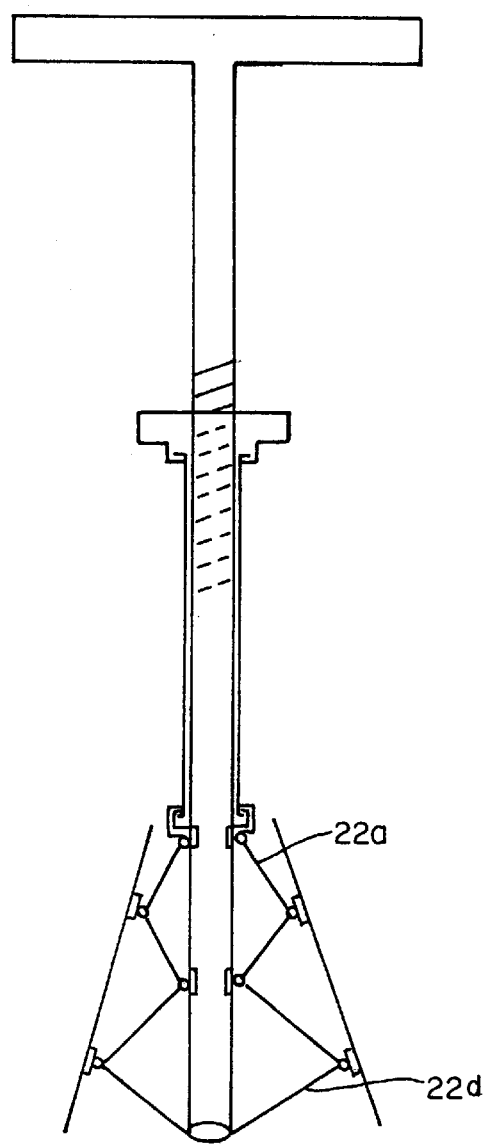
Figure 8:
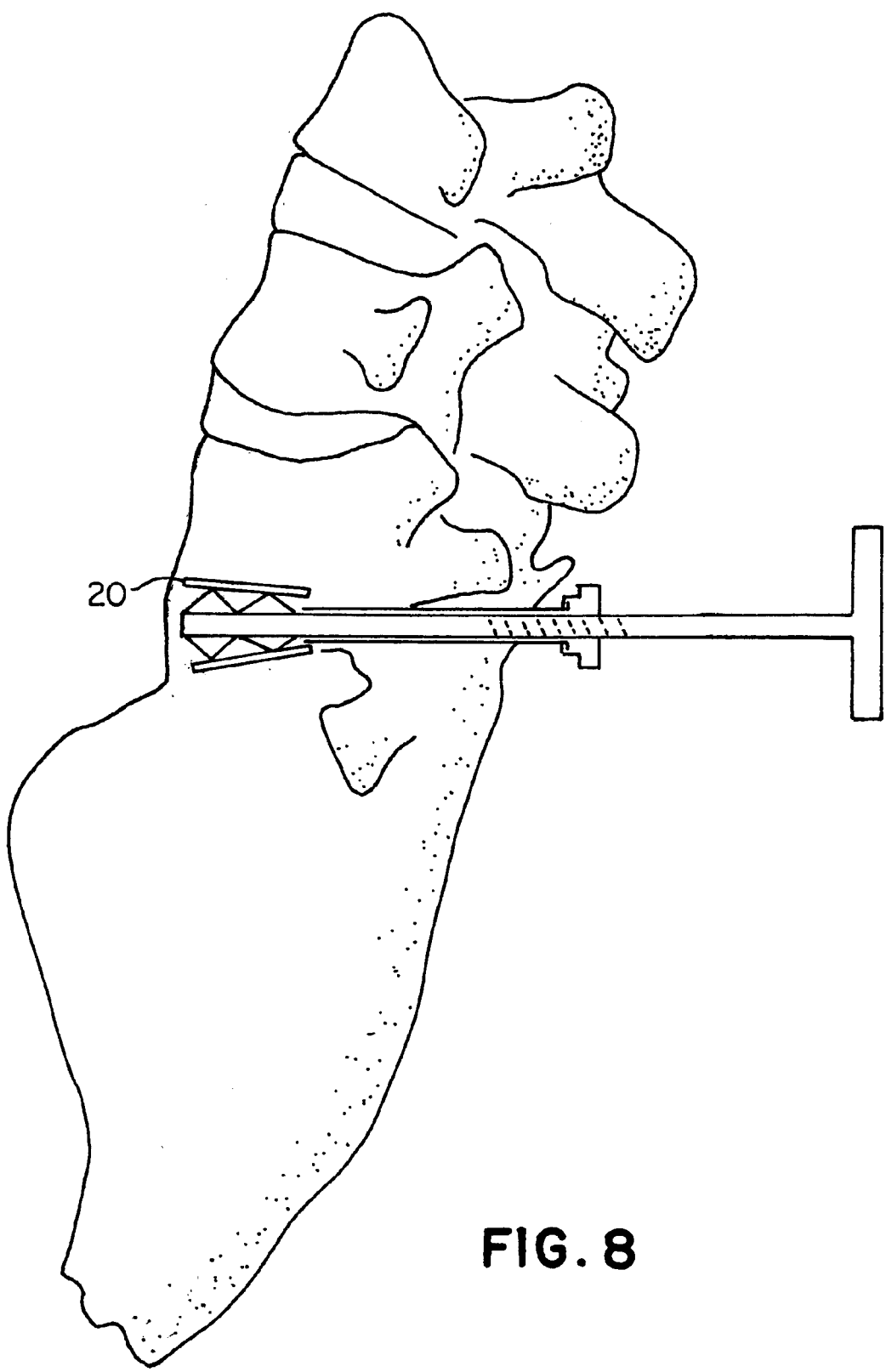
FIG. 8 shows the drill of FIG. 7b in operation.
Figure 9:
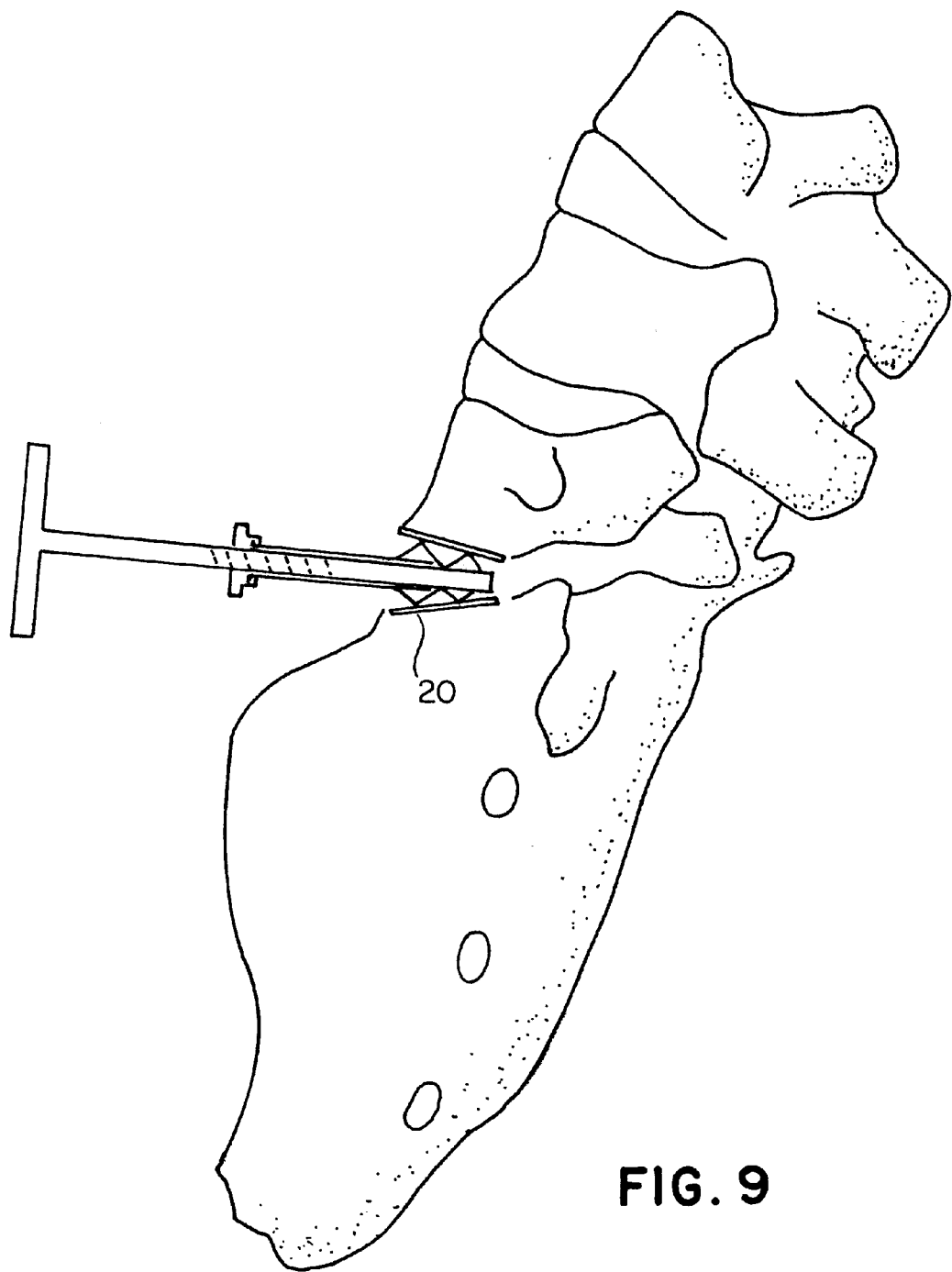
FIG. 9 shows the drill of FIG. 7a in operation.

In FIG. 3, the four links 22a, 22b, 22c, 22d have equal length, so the cutter edges are kept parallel to the shaft axis, and produce a straight hole. In FIG. 7a, the distal pair of links are shorter than the proximal links, which maintain the cutter edges at an angle that produces a tapered hole that is smaller at its bottom (FIG. 9). In FIG. 7b, the shorter links are the proximal ones, producing a hole which is larger at its bottom (FIG. 8).

Some details of the invention may change from what is described above. Since the invention is subject to modifications and variations, it is intended that the foregoing description and the accompanying drawings shall be interpreted as only illustrative of the invention defined by the following claims.

I claim:

1. An expandable orthopedic drill comprising
   a shaft having a distal end and a proximal end,
   a handle having a driving connection to the proximal end of the shaft,
   a sleeve extending around a portion of the shaft and being movable lengthwise with respect to the shaft,
   means for moving the sleeve lengthwise with respect to the shaft,
   a plurality of cutters disposed in an array around the distal end of the shaft, and
   means, operated by relative lengthwise movement between the sleeve and the shaft, for moving the cutters outward from a retracted position to an expanded position, wherein
   the shaft has an intermediate portion with external helical threads, and the means for moving the sleeve lengthwise with respect to the shaft is a nut engageable with said threads.

2. The invention of claim 1, wherein the means for moving the cutters comprises, for each cutter, a linkage including at least four links pivotally connected between the cutter and the shaft.

3. The invention of claim 2, wherein the four links are of equal length, to produce a straight hole.

4. The invention of claim 2, wherein at least some of the four links are of different lengths, to produce a tapered hole.

5. The invention of claim 1, wherein each of the cutters has a serrated cutting edge.

6. The invention of claim 1, further comprising a rotary connection between the nut and the sleeve, whereby the cutters can be retracted by unthreading the nut along the shaft.

* * * * *